US00PP36051P2

(12) United States Plant Patent
Mukundan

(10) Patent No.: US PP36,051 P2
(45) Date of Patent: Jul. 30, 2024

(54) ***AGLAONEMA* PLANT NAMED 'MUKLACY'**

(50) Latin Name: *Aglaonema hybrida*
Varietal Denomination: MUKLACY

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 18/387,305

(22) Filed: Nov. 6, 2023

(51) Int. Cl.
*A01H 5/12* (2018.01)
*A01H 6/10* (2018.01)

(52) U.S. Cl.
USPC ..... Plt./376

(58) Field of Classification Search
USPC ..... Plt./373, 376
See application file for complete search history.

(56) References Cited

U.S. PATENT DOCUMENTS

PP17,540 P2 * 3/2007 Parthasarathy ..... A01H 6/00 Plt./376
PP30,081 P2 * 1/2019 Mukundan ..... A01H 5/12 Plt./376

* cited by examiner

*Primary Examiner* — Karen M Redden
(74) *Attorney, Agent, or Firm* — C. Anne Whealy

(57) ABSTRACT

A new and distinct cultivar of *Aglaonema* plant named 'MUKLACY', characterized by its relatively compact; upright to outwardly arching plant habit; vigorous and robust growth habit; relatively short internodes giving a compact, dense, full and symmetrical plant form; large dark green-colored leaves with greyed green-colored chevrons and apical blotch and with ivory-colored margin edges and apices; strong leaf petioles that are greenish white in color; and relative tolerance to low temperatures.

2 Drawing Sheets

Figure 1:
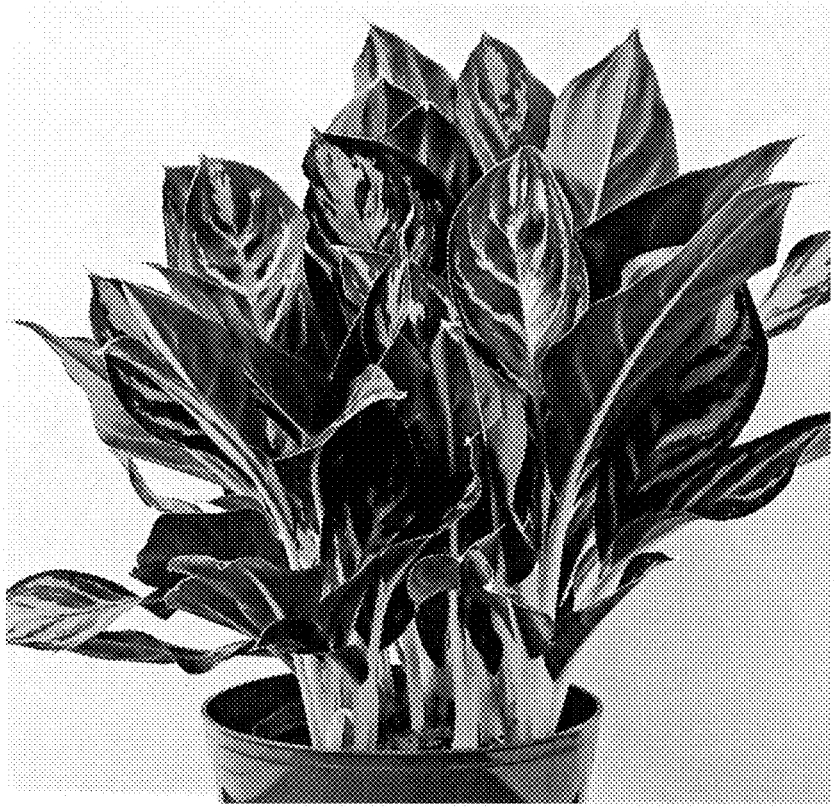

Botanical designation: *Aglaonema hybrida.*
Cultivar denomination: 'MUKLACY'.

BACKGROUND OF THE INVENTION

The present invention relates to a new and distinct cultivar of *Aglaonema* plant, botanically known as *Aglaonema hybrida* and hereinafter referred to by the name 'MUKLACY'.

The new *Aglaonema* plant is the product of a controlled breeding program conducted by the Inventor in Chamrajpet, Bangalore, India and Illalore Farm, Chennai, India. The objective of the breeding program is to create new compact and dense *Aglaonema* plants with good plant vigor, interesting and unique color and variegation patterns, resistance to pathogens and pests and tolerance to low temperatures.

The new *Aglaonema* plant is the product of a cross-pollination conducted by the Inventor on Sep. 30, 2007 in Chamrajpet, Bangalore, India of a proprietary selection of *Aglaonema hybrida* identified as code number 2007-18, not patented, as the female, or seed, parent with *Aglaonema hybrida* 'Calypso', disclosed in U.S. Plant Pat. No. 17,540, as the male, or pollen, parent. The new *Aglaonema* plant was discovered and selected by the Inventor in March, 2009 as a single plant from within the resultant progeny of the stated cross-pollination in a controlled environment at Illalore Farm, Chennai, India.

Asexual reproduction of the new *Aglaonema* plant by cuttings and divisions in a controlled environment at Illalore Farm, Chennai, India since Dec. 12, 2009 has shown that the unique features of this new *Aglaonema* plant are stable and reproduced true to type in successive generations of asexual reproduction.

SUMMARY OF THE INVENTION

Plants of the new *Aglaonema* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKLACY'. These characteristics in combination distinguish 'MUKLACY' as a new and distinct *Aglaonema* plant:

1. Relatively compact; upright to outwardly arching plant habit.
2. Vigorous and robust growth habit.
3. Relatively short internodes giving a compact, dense, full and symmetrical plant form.
4. Large dark green-colored leaves with greyed green-colored chevrons and apical blotch and with ivory-colored margin edges and apices.
5. Strong leaf petioles that are greenish white in color.
6. Relatively tolerant to low temperatures.

Plants of the new *Aglaonema* differ primarily from plants of the female parent selection in the following characteristics:

1. Plants of the new *Aglaonema* are more vigorous, faster-growing, denser and bushier than plants of the female parent selection.
2. Leaves of plants of the new *Aglaonema* are smaller and have shorter leaf petioles than leaves of plants of the female parent selection.

Plants of the new *Aglaonema* differ primarily from plants of the male parent, 'Calypso', in leaf coloration as the upper surfaces of leaves of plants of the new *Aglaonema* are dark green in color with greyed green-colored chevrons and apical blotch and with ivory-colored margin edges and apices whereas the upper leaf surfaces of plants of 'Calypso' are dark green in color with greyed green-colored chevrons interspersed with distinct golden yellow spots and blotches. In addition, plants of the new *Aglaonema* and 'Calypso' differ in leaf petiole coloration as leaf petioles of plants of the new *Aglaonema* are greenish white in color whereas leaf petioles of plants of 'Calypso' are pale yellow to ivory white in color with sparse and random green-colored spots on the petiole wings.

Plants of the new *Aglaonema* can be compared to plants of *Aglaonema hybrida* 'Mukcalsup', disclosed in U.S. Plant Pat. No. 30,081. In side-by-side comparisons, plants of the new *Aglaonema* differ primarily from plants of 'Mukcalsup', in leaf coloration as the upper surfaces of leaves of plants of the new *Aglaonema* are dark green in color with greyed green-colored chevrons and apical blotch and with ivory-colored margin edges and apices whereas the upper leaf surfaces of plants of 'Mukcalsup' are dark green-colored leaves with greyed green-colored chevrons, spots and random sectors. In addition, plants of the new *Aglaonema* and 'Mukcalsup' differ in leaf petiole coloration as leaf petioles of plants of the new *Aglaonema* are greenish white in color whereas leaf petioles of plants of 'Mukcalsup' are green white in color with numerous medium to dark green-colored spots.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet (FIG. 1) is a side perspective view of a typical plant of 'MUKLACY' grown in a container.

Figure 2:
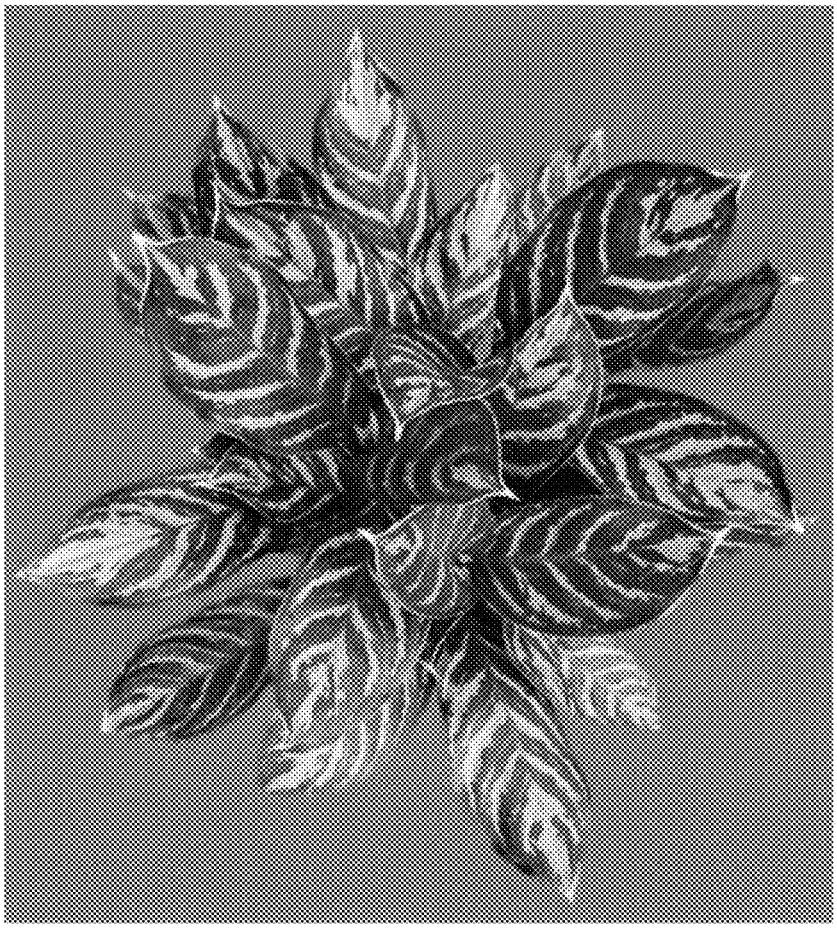

The photograph on the second sheet (FIG. 2) is a top perspective view of a typical plant of 'MUKLACY' grown in a container.

DETAILED BOTANICAL DESCRIPTION

The aforementioned photographs and following observations and measurements describe plants grown in 15-cm containers during the spring and early summer in a polyethylene-covered greenhouse in Miami, Florida. Plants were grown under environmental conditions and cultural practices which approximate those generally used in commercial *Aglaonema* production. During the production of the plants, day temperatures ranged from 25 C to 32 C and night temperatures ranged from 15 C to 23 C and 80% shade. Plants were one year old when the photographs and the detailed description were taken. In the following description, color references are made to The Royal Horticultural Society Colour Chart, 2015 Edition, except where general terms of ordinary dictionary significance are used.

Botanical classification: *Aglaonema hybrida* 'MUKLACY'.

Parentage:

*Female, or seed, parent.*—Proprietary selection of *Aglaonema hybrida* identified as code number 2007-18, not patented.

*Male, or pollen, parent.*—*Aglaonema hybrida* 'Calypso', disclosed in U.S. Plant Pat. No. 17,540.

Propagation:

*Type.*—By top cuttings, stem cuttings and divisions.

*Time to initiate roots, summer.*—About 20 to 25 days at temperatures about 25 C to 35 C.

*Time to initiate roots, winter.*—About 35 to 40 days at temperatures about 30 C to 35C.

*Time to produce a rooted young plant, summer.*—About 45 to 50 days at temperatures about 25 C to 35C.

*Time to produce a rooted young plant roots, winter.*—About 50 to 55 days at temperatures about 15 C to 20 C.

*Root description.*—Medium in thickness, fibrous; typically off-white in color, actual color of the roots dependent on substrate composition, water quality, fertilizer, substrate temperature and age of roots.

*Rooting habit.*—Freely branching; dense.

Plant description:

*Plant and growth habit.*—Relatively compact; upright to outwardly arching plant habit; vigorous and robust growth habit; relatively short internodes giving a compact, dense, full and symmetrical habit; developing leaves initially upright, then arching outwardly with development on strong petioles.

*Plant height, from soil level to top of leaf plane.*—About 46.5 cm.

*Plant diameter or spread.*—About 61.5 cm.

*Stem description.*—Aspect: Mostly upright. Strength: Strong, sturdy; slightly flexible. Diameter, at the base: About 2.6 cm. Internode length, at the base: About 1.5 cm. Color: Closest to 193C and 193D; at the nodes, close to 147A.

Leaf description:

*Arrangement.*—Alternate to whorled; simple.

*Length.*—About 33 cm.

*Width.*—About 13.5 cm.

*Shape.*—Broadly lanceolate to oblanceolate.

*Apex.*—Acuminate with cuspidate tendencies; recurved.

*Base.*—Attenuate.

*Margin.*—Entire; slightly and coarsely undulate.

*Texture and luster, upper surface.*—Smooth, glabrous; initially glossy and becoming moderately glossy with development.

*Texture and luster, lower surface.*—Smooth, glabrous; initially moderately glossy and becoming slightly glossy with development.

*Venation pattern.*—Pinnate.

*Color.*—Developing and fully expanded leaves, upper surface: Ground color, closest to between 147A and 139A; chevrons and apical blotch, closest to 191A to more green than 191A; marginal edges and at the apex, closest to 157A; midvein, closest to between 147A and 139A; lateral venation, similar to lamina colors. Developing and fully expanded leaves, lower surface: Closest to 146A to 146B to more green than 146A to 146B; midvein, closest to 155C; lateral venation, similar to lamina colors.

*Petioles.*—Aspect: Mostly erect to outwardly arching with development; about 45 degrees from vertical. Length: About 17 cm. Diameter, distal: About 7 mm by 9 mm. Diameter, proximal: About 1.2 cm by 1.6 cm. Strength: Strong; flexible. Color: Closest to 155C and 157A to 157B. Wing length: About 14.5 cm. Wing diameter, base: About 9 mm. Wing texture: Smooth, glabrous; towards the margin, membraneous. Wing color, inner and outer surfaces: Closest to 155C and 157A to 157B.

Inflorescence description: Inflorescence development has not been observed on plants of the new *Aglaonema* to date.

Pathogen & pest resistance: Plants of the new *Aglaonema* have not been observed to be resistant to pathogens or pests common to *Aglaonema* to date.

Temperature tolerance: Plants of the new *Aglaonema* have been observed to be relatively low temperature tolerant and to tolerate temperatures ranging from about 10 C to about 38 C.

It is claimed:

1. A new and distinct *Aglaonema* plant named 'MUKLACY' as illustrated and described.

* * * * *